United States Patent
Hudgins et al.

(10) Patent No.: US 6,458,313 B2
(45) Date of Patent: *Oct. 1, 2002

(54) METHOD FOR REDUCING DILATION BALLOON CONE STIFFNESS

(75) Inventors: R. Garryl Hudgins, Lino Lakes, MN (US); Robert C. Farnan, Flagstaff, AZ (US)

(73) Assignee: Schneider (USA) Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/907,989

(22) Filed: Jul. 18, 2001

Related U.S. Application Data

(63) Continuation of application No. 09/112,532, filed on Jul. 9, 1998, now Pat. No. 6,287,506.

(51) Int. Cl.[7] .......................... B29C 49/04; B29C 49/08
(52) U.S. Cl. ...................... 264/515; 264/532; 264/573; 264/900; 604/96; 606/194
(58) Field of Search .................. 264/515, 532, 264/573, 900; 604/96; 606/194

(56) References Cited

U.S. PATENT DOCUMENTS

| | | | |
|---|---|---|---|
| 4,154,244 A | 5/1979 | Becker et al. | 128/349 B |
| 4,254,774 A | 3/1981 | Boretos | |
| 4,331,786 A | 5/1982 | Foy et al. | |
| 4,332,920 A | 6/1982 | Foy et al. | |
| 4,385,635 A | 5/1983 | Ruiz | |
| 4,413,989 A | 11/1983 | Schjeldahl et al. | 604/96 |

(List continued on next page.)

FOREIGN PATENT DOCUMENTS

| | | |
|---|---|---|
| EP | 88300025.9 | 5/1988 |
| EP | 274 411 | 7/1988 |
| EP | 89118420.2 | 10/1989 |
| EP | 0 485 903 | 5/1992 |

OTHER PUBLICATIONS

Flesher, Polyether block, amide, high–performance TPE, Modern Plastics, Sep. 1987, pp. 100, 105, 110.
Koch, "PEBAX (Polyether Block Amide)", Advances in Polymer Technology, vol. 2, No. 3 1982 pp. 160–162.
De, et al. eds. *Thermoplastic Elastomer From Rubber–Plastic Blends, Chapter 1,* Ellis Horwoal, New York pp. 13–27.
Gorski, The Nomenclature of Thermoplastic Elastomers, Kunstoffe German Plastics, 83 (1993) No. 3, pp. 29–30.
Hofman, Thermoplastic Elastomers, Kunstoffe German Plastics, 80 (1990) No. 10, pp. 88–90.
Atochem, "Pebax Resins 33 Series Property Comparison" undated, (1 pg. manufacturers technical information sheet received Sep. 29, 1994).
Atochem, undated and untitled brochure for Pebax resins, pp. 2–5.
Bhowmick, et al eds. *Handbook of Elastomers,* Chapters 10 and 12, Marcel Dekker Inc., pp. 341–373 and 411–442.
Walker, et al, eds. *Handbook of Thermoplastic Elastomers,* Chapter 8, Van Nostrand Reinhold Co., NY pp. 258–281.

*Primary Examiner*—Suzanne E. McDowell
(74) *Attorney, Agent, or Firm*—Vidas, Arrett & Steinkraus, PA

(57) ABSTRACT

A method for stretch blow molding dilatation balloons for angioplasty catheters having a significantly reduced cone thickness without sacrifice in burst strength is achieved by utilizing a mold whose cavity includes arcuate walls defining the balloon's end cones and a predetermined minimal distance from the side edges of the mold to the points where the arcuate walls intersect with a smaller diameter balloon stem portion. Utilizing this mold and providing for three longitudinal stretching sequences, one prior to, one during and one following radial expansion of the heated plastic parison, results in an improved balloon exhibiting reduced cone stiffness.

13 Claims, 3 Drawing Sheets

U.S. PATENT DOCUMENTS

| | | | |
|---|---|---|---|
| 4,490,421 A | 12/1984 | Levy | 428/35 |
| 4,563,181 A | 1/1986 | Wijaymathna | |
| 4,675,361 A | 6/1987 | Ward, Jr. | 525/92 |
| 4,786,556 A | 11/1988 | Hu et al. | 428/412 |
| RE32,983 E | 7/1989 | Levy | |
| 4,886,506 A | 12/1989 | Lovgren et al. | |
| 4,898,591 A | 2/1990 | Jang et al. | |
| 4,906,244 A | 3/1990 | Pinchuck et al. | |
| 4,917,667 A | 4/1990 | Jackson | |
| 4,938,676 A | 7/1990 | Jackoski et al. | 425/140 |
| 4,950,239 A | 8/1990 | Gahara et al. | 604/96 |
| 4,950,257 A | 8/1990 | Hibbs et al. | |
| 4,952,357 A | 8/1990 | Euteneuer | 264/129 |
| 4,963,133 A | 10/1990 | Whipple | 604/283 |
| RE33,561 E | 3/1991 | Levy | |
| 5,087,394 A | 2/1992 | Keith | |
| 5,195,969 A | 3/1993 | Wang et al. | 604/96 |
| 5,250,069 A | 10/1993 | Nobuyoshi et al. | |
| 5,270,086 A | 12/1993 | Hamlin | 428/35 |
| 5,281,677 A | 1/1994 | Onwunaka et al. | 525/458 |
| 5,290,306 A | 3/1994 | Trotta et al. | 606/194 |
| 5,295,978 A | 3/1994 | Fan et al. | 604/265 |
| 5,300,048 A | 4/1994 | Dewes, Jr. et al. | 604/280 |
| 5,304,134 A | 4/1994 | Kraus et al. | 604/96 |
| 5,328,468 A | 7/1994 | Kaneko et al. | 604/96 |
| 5,335,675 A | 8/1994 | Wheeler et al. | 128/842 |
| 5,344,400 A | 9/1994 | Kaneko et al. | 604/96 |
| 5,348,538 A | 9/1994 | Wang et al. | 604/96 |
| 5,397,306 A | 3/1995 | Nobuyoshi et al. | 604/96 |
| 5,478,320 A | 12/1995 | Trotta | 604/96 |
| 5,512,051 A | 4/1996 | Wang et al. | 604/96 |
| 5,556,383 A | 9/1996 | Wang et al. | 604/96 |
| 5,645,789 A | 7/1997 | Roucher, Jr. | |
| 5,714,110 A * | 2/1998 | Wang et al. | 264/532 |
| 5,738,653 A | 4/1998 | Thomas et al. | |
| 5,948,345 A * | 9/1999 | Patel et al. | 264/573 |
| 6,287,506 B1 | 9/2001 | Hudgins et al. | |

FOREIGN PATENT DOCUMENTS

| | | |
|---|---|---|
| EP | 0513 459 A1 | 11/1992 |
| EP | 420 488 B | 7/1993 |
| EP | 0 566 755 A1 | 10/1993 |
| EP | 566 755 A | 10/1993 |
| EP | 540 858 A | 12/1993 |
| EP | 0 592 885 | 4/1994 |
| EP | 0 730 879 | 9/1996 |
| FR | 2 651 681 | 3/1991 |
| WO | 84/01513 | 4/1984 |
| WO | 92/8512 | 5/1992 |
| WO | 92/19316 | 11/1992 |
| WO | WO 23619 | 9/1995 |
| WO | 95/23619 | 9/1995 |
| WO | 96/04951 | 2/1996 |
| WO | WO 96/12516 | 5/1996 |
| WO | WO 97/03716 | 2/1997 |

* cited by examiner

METHOD FOR REDUCING DILATION BALLOON CONE STIFFNESS

CROSS-REFERENCE TO RELATED APPLICATIONS

This application is a Continuation Application claiming priority from U.S. application Ser. No. 09/112,532 filed Jul. 9, 1998, now U.S. Pat. No. 6,287,506, the entire contents of which being incorporated herein by reference.

BACKGROUND OF THE INVENTION

I. Field of the Invention

The present invention relates to dilatation balloon catheters of the type employed in percutaneous transluminal angioplasty procedures, and more particularly to a method of molding such balloons to reduce their cone stiffness and thereby improve the maneuverability in smaller and more tortious passages of the vascular system.

II. Discussion of the Prior Art

Dilatation balloon catheters are well known for their utility in treating the build-up of plaque and other occlusions in blood vessels. Typically, a catheter is used to carry a dilatation balloon to a treatment site, where fluid under pressure is supplied to the balloon, to expand the balloon against a stenotic lesion.

The dilatation balloon is affixed to an elongated flexible tubular catheter proximate its distal end region. When the balloon is expanded, its working length, i.e., its medial section, exhibits a diameter substantially larger than that of the catheter body on which it is mounted. The proximal and distal shafts or stems of the balloon have diameters substantially equal to the diameter of the catheter body. Proximal and distal tapered sections, referred to herein as "cones", join the medial section to the proximal and distal shafts, respectively. Each cone diverges in the direction toward the medial section. Fusion bonds between the proximal and distal balloon shafts and the catheter form a fluid-tight seal to facilitate dilation of the balloon when a fluid under pressure is introduced into it, via an inflation port formed through the wall of the catheter and in fluid communication with the inflation lumen of the catheter.

Along with body tissue compatibility, primary attributes considered in the design and fabrication of dilation balloons are their strength and pliability. A higher hoop strength or burst pressure reduces the risk of accidental rupture of the balloon during dilation. Pliability refers to formability into different shapes, rather than elasticity. In particular, when delivered by the catheter, the dilatation balloon is evacuated, flattened and generally wrapped circumferentially about the catheter in its distal region. Thin, pliable dilatation balloon walls facilitate a tighter wrap that minimizes the combined diameter of the catheter and the balloon during delivery. Furthermore, pliable balloon walls enhance the catheter "trackability" in the distal region, i.e., the ability of the catheter to bend in conforming to the curvature in vascular passages through which it must be routed in reaching a particular treatment site.

One method of forming strong, pliable dilatation balloons of polyethylene terrathalate (PET) is disclosed in U.S. Pat. No. RE. 33,561 (Levy). A tubular parison of PET is heated at least to its second order transition temperature, then drawn to at least triple its original length to axially orient the tubing. The axially expanded tubing is then radially expanded within a heated mold to a diameter about triple the original diameter of the tubing. The form of the mold defines the aforementioned medial section, shafts and cones, and the resulting balloon has a burst pressure greater than 200 psi.

Such balloons generally have a gradient in wall thickness along the cones. In particular, larger dilatation balloons, e.g., 3.0–4.0 mm diameter (expanded) tend to have a wall thickness in the working length in the range of from 0.010 to 0.020 mm. Near the transition of the cones with the working length or medial section, the cones have approximately the same wall thickness. However, the wall thickness diverges in the direction away from the working length, until the wall thickness near the proximal and distal shafts is in the range of 0.025 to 0.040 mm near the associated shaft or stem.

The increased wall thickness near the stems does not contribute to balloon hoop strength, which is determined by the wall thickness along the balloon medial region. Thicker walls near the stems are found to reduce maneuverability of the balloon and catheter through a tortious path. Moreover, the dilatation balloon cannot be as tightly wrapped about the catheter shaft, meaning its delivery profile is larger and limiting the capacity of the catheter and balloon for treating occlusions in smaller blood vessels.

U.S. Pat. No. 4,963,133 (Noddin) discloses an alternative approach to forming a PET dilation balloon, in which a length of PET tubing comprising the parison is heated locally at opposite ends and subjected to axial drawing to form two "necked-down" portions, which eventually become the opposite ends of the completed balloon. The necked-down tubing is then simultaneously axially drawn and radially expanded with a gas. The degree to which the tubing ends had been necked-down is said to provide control over the ultimate wall thickness along the walls defining the cones. However, it is believed that the use of the Noddin method results in balloons exhibiting a comparatively low burst pressure.

Copending application Ser. No. 08/582,371, filed Jan. 11, 1996, now U.S. Pat. No. 5,733,301, describes a method for reducing cone stiffness by using a laser to ablate and remove polymeric material from the cone areas after the balloon is blown. It is preferable that the desired result be obtained during the balloon molding operations obviating the need for additional post molding operations.

Therefore, it is an object of the present invention to provide a method for stretch blow molding dilatation balloon having a high burst pressure and hoop strength, but with reduced material mass in the balloon cones, thus reducing cone stiffness and improving the trackability, crossing profile, stenosis recross and balloon retrieval, via a guiding catheter.

SUMMARY OF THE INVENTION

To achieve these and other objects of the invention, there is provided a method of making dilatation balloons with reduced cone stiffness. The method comprises the steps of first providing a mold having a cavity including a cylindrical center segment defining a working length of a dilatation balloon body where the center segment is of a predetermined diameter. The mold cavity also includes two opposed end segments, each having an arcuate cone shape tapering from the predetermined diameter of the center segment to a smaller desired balloon shaft diameter. The side edges of the mold are dimensioned to be within about 0.05 in. of the termination point of the arcuate cone at the smaller desired balloon shaft diameter.

Next, a tubular polymeric parison of a predetermined diameter and wall thickness is placed with a mold and the parison has the opposed ends thereof extending beyond the side edges of the mold, the opposed ends being clamped in a tensioning fixture. The mold is heated to bring the temperature of the parison near or above the glass transition temperature of the polymeric material comprising the parison. The tensioning fixture is then longitudinally displaced relative to the mold to initially longitudinally stretch the parison by a predetermined amount to introduce a degree of longitudinal orientation and to neck down the tubular parison to a lesser diameter.

Following this initial longitudinal stretch, a second longitudinal stretching operation is initiated and as the tensioning fixture is being moved to achieve a second stretch, a gas is injected into the tubular parison to radially expand the parison to a limit defined by the mold cavity. At this point, the wall thickness in the working length of the balloon and in its cones is a function of the degree of longitudinal and radial stretching as well as the gas pressure applied to effect the radial expansion.

Following inflation of the balloon within the mold, a third longitudinal stretch is performed by further displacing the tensioning fixtures relative to the mold. It is the third stretch within the above-described mold that is found to remove material from the cone area as the tubing is drawn down to a desired size for a catheter shaft. Removal of material from the cone area renders them more pliable than balloons prepared in the same way but not subjected to longitudinal stretching following the radial expansion of the balloon within the mold. The third stretch also creates an increased number of nucleation sites for crystallization to occur.

After the third stretch operation is terminated, the temperature of the mold is increased such that the biaxially oriented balloon reaches its crystallizing temperature for effectively locking the molecular structure in place.

Following crystallization, the mold is cooled below the glass transition temperature of the polymer so that the crystallization structure of the balloon is not lost. Once the mold has sufficiently cooled, it can be opened and the balloon removed.

DESCRIPTION OF THE DRAWINGS

FIG. 3 is a drawing helpful in understanding the manner in which the mold cavity shape is arrived at.

DESCRIPTION OF THE PREFERRED EMBODIMENT

Figure 1:
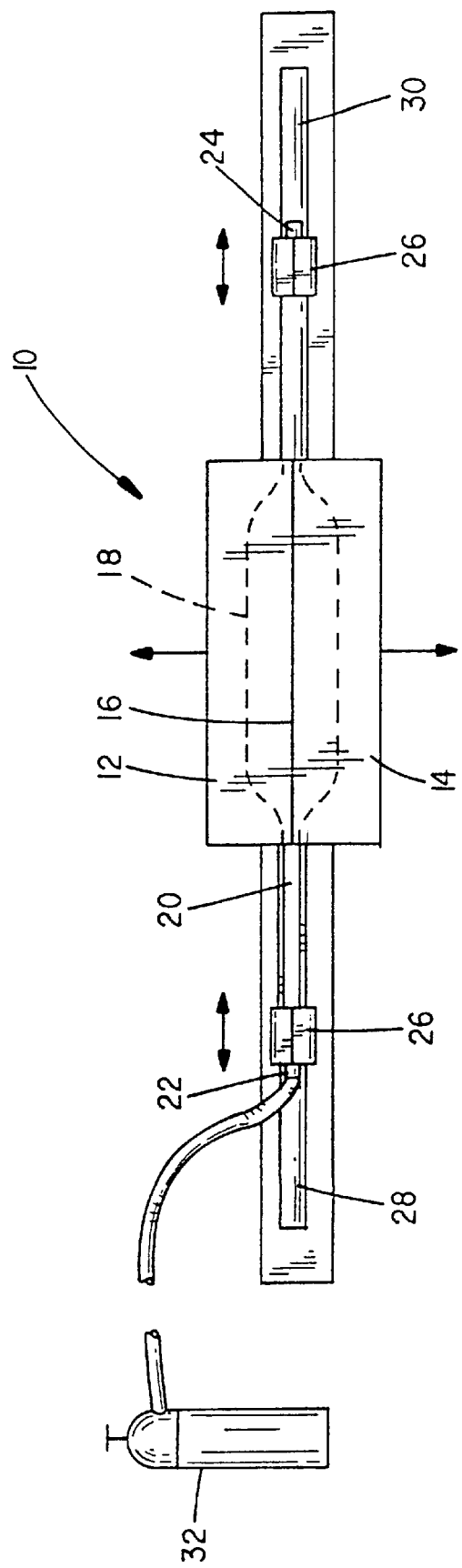
FIG. 1 is a top elevational schematic view of the equipment used in carrying out the method of the present invention.

Referring to FIG. 1, there is illustrated schematically the apparatus for stretch blow molding dilatation balloons for later assembly on to catheter body stock in the fabrication of dilatation balloon catheters. The mold itself is indicated generally by numeral 10 and comprises first and second mold halves 12 and 14 which when abutting one another at a parting line 16 define an internal mold cavity 18. The mold halves or jaws can be open or spread apart to allow placement of a tubular parison therein. The opposed ends of the parison 22 and 24 are clamped in a tensioning fixture including clamping jaws 26 which are mounted on rails 28 and 30 for longitudinal movement therealong.

As those skilled in the art appreciate, the mold 10 incorporates heating elements (not shown) and appropriately positioned temperature sensors for monitoring the mold temperature and sending temperature information back to a microprocessor-based controller for maintaining precise closed-loop control of the temperature of the mold and of the parison contained in it. Likewise, a suitable linear encoder (not shown) is operatively coupled to the translatable clamping fixtures 26 to provide positional information to the microprocessor-based controller whereby the degree of longitudinal stretch imparted to the parison 20 can be precisely controlled.

The equipment for stretch blow molding shown in FIG. 1 also includes a means for introducing a gas 32, under pressure, into the lumen of the tubular parison 20 and for monitoring and controlling that pressure again, using closed-loop control.

Except for the mold cavity 18 formed in the mold halves 12 and 14, the equipment used in carrying out the method of the present invention is altogether conventional. The mold cavity employed is unique, as is the operation whereby the cone segments of the balloons to be formed in it are made to contain less material than in conventional designs.

Figure 2:
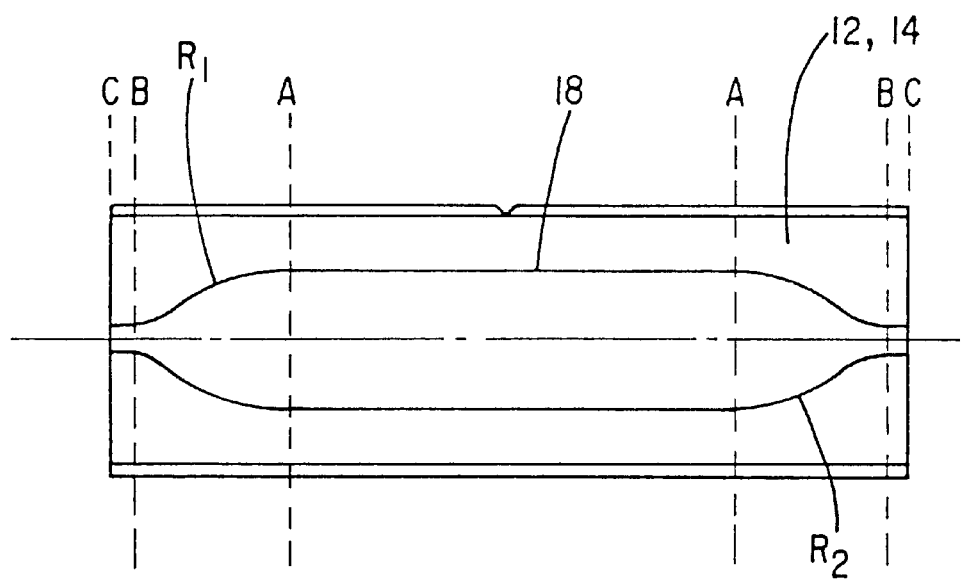
FIG. 2 is an enlarged view of one of the jaws of the mold showing the desired profile of the mold cavity used in preparing dilatation balloons having reduced cone stiffness.

FIG. 2 is a view looking at the interior of one of the jaws 12 or 14 and showing the preferred profile of the mold cavity 18.

The portion of the balloon between the dashed construction lines A—A define the working length of a dilatation balloon formed therein and this portion of the balloon is generally cylindrical. The portion of the mold between construction lines A and B form the cones and, as can be seen from FIG. 2, the cones do not have a linear taper. They are slightly arcuate in the zone between the construction lines A and B. The portion of the mold between the construction lines B and C will ultimately comprise the shaft portion of the balloon formed in the mold cavity 18.

The following table sets out typical mold dimensions in stretch blow-molding a dilatation balloon having a working length of 20 mm and an expanded diameter of 4.0 mm. These dimensions are illustrative only because the various dimensions change depending upon the size of the balloon to be formed.

TABLE I

| Dimension | Magnitude (Inches) |
| --- | --- |
| A-A | .763 |
| B-B | 1.532 |
| C-C | 1.557 |
| B-C | .025 |
| A-B | .372 |
| $R_1$ | .832 |
| $R_2$ | 1.010 |

Figure 3:
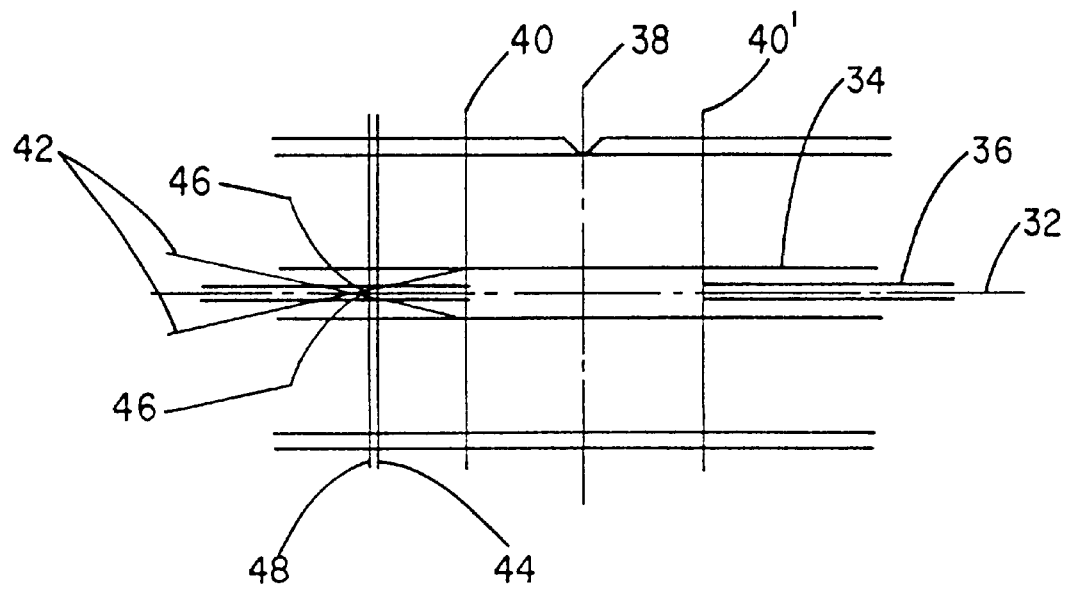

With reference to FIG. 3, for any size balloon diameter, the radiused balloon ends of the mold are designed using the following graphical construction technique:

1. The horizontal centerline 32 for the mold is first established.

2. Construction lines 34 above and below the horizontal center line 32 are established to define the desired balloon diameter.

3. Construction lines 36 above and below the center line establish the desired balloon shaft diameters for both the proximal and distal ends.

4. The vertical center line 38 for the mold is set.

5. Lines 40 and 40' define the desired working length of the balloon body on either side of the vertical center line 38.

6. Construction lines 42 are created at the points of intersections of lines 36 and 40 such that lines 42 form a desired angle with respect to line 36. An angle of 12° is typical. Each of lines 42 should cross the horizontal center line 32 of the mold. Construction lines 42 determine the length of the end of the balloon.

7. Construction line 44 is created at the intersection of lines 36 and 42. Construction line 44 indicates the boundary for the end of the balloon and the transition to the balloon shaft.

8. Arcs 46 are next constructed. Arc 46 is a three point arc, and it should pass through the intersection of lines 34 and 40, and lines 42 and 44. The end point of the arcs 46 should be chosen so that they are tangent to line 34 at the intersection of lines 34 and 40.

9. Construction lines 42 can now be erased and the portion of the arcs 46 to the left (outside) of construction line 44 can also be erased.

10. Displace construction line 44 to the left by 0.025 in. to 0.25 in. establish the left end of the mold which is depicted in FIG. 3 by construction line 48.

11. The lines 36 to the right (inside) of construction line 44 and to the left (outside) of construction line 48 are trimmed to form the short land of the mold.

12. Construction line 44 can now be erased and lines 34 trimmed to the left (outside) of line 40 of the left half of the mold.

13. The foregoing construction steps are then repeated for the right side of the mold to form the other balloon end.

As will be explained in further detail hereinbelow, by providing the arcuate cone segments and the short cylindrical shaft segments (dimension B-C in Table I), it is possible to remove polymeric material from the cone portions of the mold by providing a third stretch to the parison following inflation of the parison to achieve radial orientation.

Figure 4:
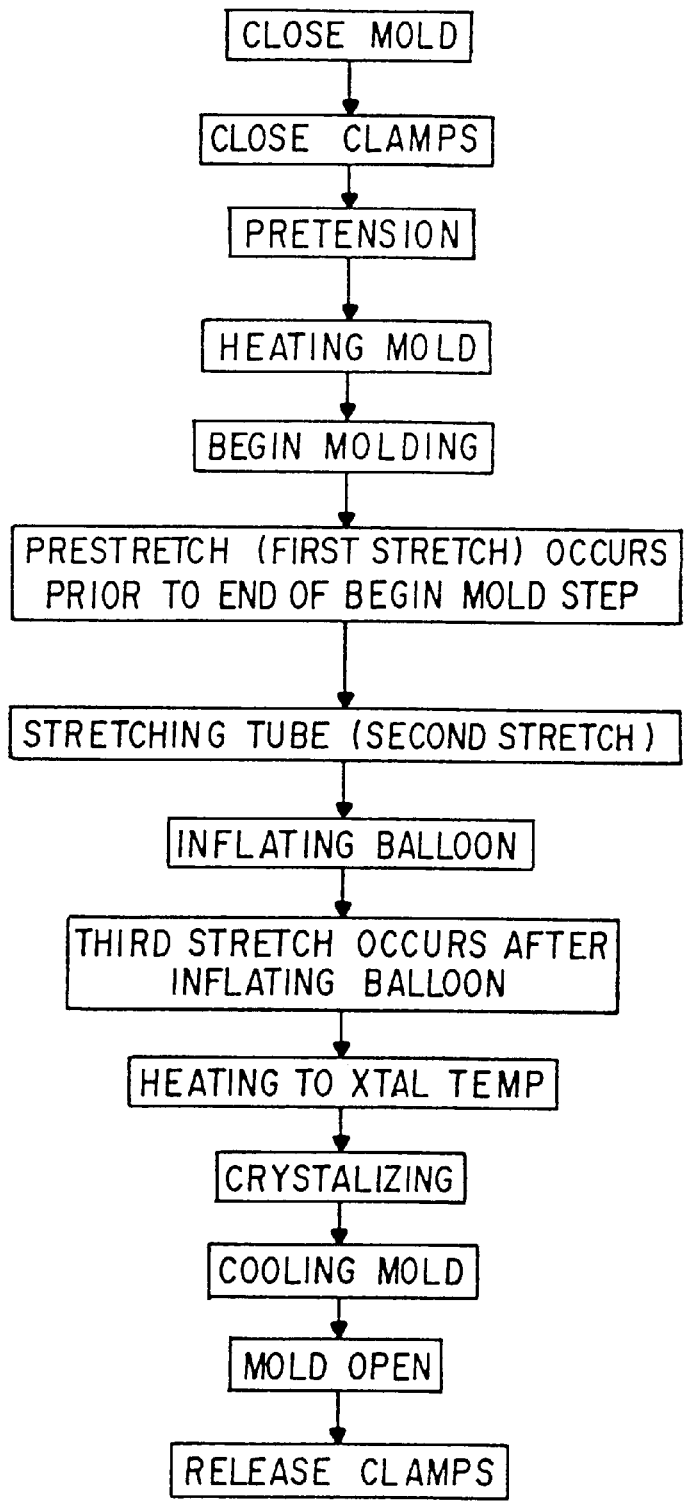
FIG. 4 is a flow chart of the steps employed in preparing dilatation balloons exhibiting reduced cone stiffness.

Using the mold created using the techniques outlined above in the apparatus of FIG. 1, dilatation balloons exhibiting a reduced cone thickness as compared to prior art stretch blow molding operations can be achieved. Referring to FIG. 4, there is illustrated a flow chart of the steps used to prepare such improved dilatation balloons. In carrying out the method, a precut length of a suitable tubular parison is placed in the mold so as to span the mold cavity in the longitudinal direction. The opposed ends of the parison are clamped by the tensioning member 26. The mold is partially closed about the tubular parison 20 and a gas at a relatively low pressure is introduced into the lumen of the parison and a slight tension is applied to eliminate sagging of the parison when subsequently heated.

Following this initial setup and pretensioning, the mold 10 is heated up to a desired temperature which depends upon the thermoplastic material involved. Generally speaking, the mold is heated to a temperature which is above the glass transition temperature. For PET, the mold may typically be heated to 175°. Once this temperature is reached, the molding operation can be begin.

The parison is subjected to a first stretching operation to initiate longitudinal orientation in the plastic. The degree of stretch varies with the tube size (wall thickness) and the tube material. This first stretch which for a PET parison may be in the range of ¼ in. to 1-½ in. at each end thereof, not only results in some longitudinal orientation, but it also necks down the original tubing comprising the parison to a smaller diameter.

After the prestretch (first stretch), the mold is completely closed and a second longitudinal stretch is initiated. During the time that the second stretch is occurring, the balloon is fully inflated by injecting an inert, dry gas, e.g., nitrogen, under relatively high pressure into the lumen of the parison to thereby radially expand the parison to fill the mold. The gas pressure depends on tubing thickness and the desired wall thickness of the resulting balloon but will typically be in the range of from 50 psi to about 400 psi. The wall thickness of the resulting balloon is a function of both the longitudinal stretch and the radial stretch employed. There is also an interaction between the pressure and the degree of longitudinal stretch on the thickness of the resulting balloon wall. Generally speaking, the higher the pressure, the less the wall is thinned by the longitudinal strecthing.

With continued reference to the flow chart of FIG. 4, following inflation of the balloon and while the balloon is still subjected to the pressure of the inflation gas, the parison is longitudinally stretched a third time. Because of the arcuate shape of the mold in the zone thereof defining the end cones and because of the short dimension B-C (FIG. 2 and Table I), the third longitudinal stretch is effective to remove material from the cone area of the balloon and to simultaneously draw the tubing down to a desired size thereby providing a thinner shaft portion for later attachment to the catheter body.

Defining the stretch ratio as the ratio of the length after the stretch divided by the length prior to the stretch, for a PET polymer the first stretch ratio may be in the range of from 1.005 to 2.0, that for the second stretch in the range of from 1.05 to 3.0 and for the third stretch in the range of from 1.1 to 4.0.

Following the third stretch operation, the temperature of the mold is increased to the crystallizing temperature of the polymer employed to effectively "freeze" the molecular structure resulting from the longitudinal and radial orientation in place. The crystallizing step takes place with the balloon pressurized to the same inflation pressure earlier applied during the balloon inflation step. This helps to ensure that the balloon walls in the working area will remain at the same thickness after the third longitudinal stretch and subsequent crystallizing.

The mold can now be cooled down back below the glass transition temperature for the polymer and, following that, the mold can be opened and the clamps released. The portion of the parison outside of the mold is then trimmed off and the balloon is ready to be mounted on a catheter body.

Comparative tests were run on balloons prepared in accordance with the method of FIG. 4 when using a mold having a profile like that of FIG. 2 with balloons fabricated using a prior art "two stretch" molding process having all of the steps of FIG. 4 except the third stretch following balloon inflation and in a mold that had linear (rather than arcuate) cone profiles. These specific parameters that were compared were derived by advancing a plurality of dilatation catheters having balloons manufactured in accordance with the method of the present invention and balloons manufactured in accordance with the described prior art through a test fixture. The test fixture had a tortuous path and located at differing spots within the tortuous path were a Palmez-Schatz stent and a Wallstent® Endoprosthesis. The purpose of this test was to evaluate the forces required to push the catheter through the fixture and the ability of the catheter to pass through each of the stents without getting caught by the stent's structure. The average force that was required to pass the conventional catheter through the test fixture was 695.9 grams. This is to be compared with 390.5 grams required to be applied to the catheters having balloons made in accordance with the present invention to traverse the same test fixture. This represents approximately a 44 percent reduction in tracking force.

A further test was conducted to assess the force required to re-cross a stenosis following balloon inflation. Balloons made in accordance with the method of the present invention in the mold cavity made as described herein showed an approximate decrease of 18 percent in the stenosis recross force when compared to balloons molded in the conventional "two stretch" process.

Testing further revealed that the balloons molded with the "three stretch" process of the present invention required the lowest force to withdraw the balloon catheter through a guiding catheter. The force to withdraw the balloons prepared in the three stretch process was about 28% less than the force necessary to withdraw balloons made using the prior art two stretch process.

Balloons made in accordance with the three stretch process of the present invention were able to be guided through the stent blocks. The conventional balloons made using the two stretch process were not capable of being pushed through the stents, even with considerable effort.

The improved performance of dilatation balloons made in accordance with the present invention is believed to be due to the extraction of material from the cone areas of the balloon taking place during the third stretch. The process of the present invention produces a high degree of molecular orientation, yielding balloons with high strength and simultaneously a reduced balloon wall thickness, balloon cone thickness and balloon shaft diameter. This eliminates the need for subsequent balloon processing following the balloon blowing operation.

What is claimed is:

1. A method of making dilatation balloons with reduced cone stiffness, comprising the steps of:
   (a) providing a mold having a cavity therein including a center section of a predetermined diameter defining a working length for a balloon to be formed therein and opposed end cone segments, each defined by an arcuate wall tangent to a wall defining the generally cylindrical center section and terminating in a cylindrical end segment corresponding to a desired shaft size for the balloon to be formed therein, the mold having opposed side edges spaced less than 0.25 inch from a point of intersection of the arcuate wall and the cylindrical end segment;
   (b) placing a tubular parison of a predetermined polymeric composition across the mold cavity, the tubular parison having opposed ends extending outwardly from the opposed side edges of the mold;
   (c) clamping the opposed ends of the tubular parison in longitudinally displaceable tensioning fixtures;
   (d) heating the mold to a temperature above the glass transition temperature of the polymeric composition of the parison;
   (e) longitudinally displacing the tensioning fixtures relative to the mold a first time to effect a first predetermined stretch ratio;
   (f) subsequently longitudinally displacing the tensioning fixture relative to the mold a second time to effect a second predetermined stretch ratio while simultaneously injecting a gas, under pressure, into the tubular parison to radially expand the parison against the walls defining the mold cavity and thereby form a balloon having a generally cylindral center segment, a pair of opposed cone segments and a pair of opposed shaft segments;
   (g) further longitudinally displacing the tensioning fixture relative to the mold a third time to effect a third stretch ratio, the spacing of the opposed ends of the mold and the arcuate wall configuration of the mold end cone segments configured to affect selective thinning of the balloon cone and shaft segments;
   (h) cooling the mold to a temperature below the glass transition temperature of the polymeric composition; and
   (i) removing the resulting balloon from the mold.

2. The method as in claim 1 and further including a step of pretensioning the tubular parison prior to step (d).

3. The method as in claim 1 wherein the polymeric composition comprises PET.

4. The method as in claim 3 wherein the first predetermined stretch ratio is in a range of from 1.005 to 2.0.

5. The method as in claim 3 wherein the second predetermined stretch ratio is in a range of from 1.05 to 3.0.

6. The method as in claim 3 wherein the third stretch ratio is in a range of from 1.1 to 4.0.

7. The method as in claim 1 wherein the tubular parison is a co-extrusion of Nylon 12 over PET.

8. The method as in claim 1 wherein the gas injected is at a pressure in a range of from 50 psi to 400 psi.

9. The method as in claim 1, further comprising the step of heating the mold to the crystallizing temperature of the polymeric composition prior to cooling the mold.

10. A method of fabricating a dilatation balloon in a stretch blow molding operation comprising the steps of:
   (a) providing a mold having a cavity formed therein defining a desired shape configuration of a dilatation balloon to be formed therein, the mold including a cylindral central section and opposed generally conical end sections tapering to a reduced diameter shaft segment, each shaft segment extending axially to a side edge, wherein the generally conical end sections comprise arcuate boundaries defining the opposed generally conical end sections;
   (b) placing a tubular parison of a polymeric composition having a predetermined diameter and wall thickness across the mold with opposed ends of the parison extending outward beyond the side edges of the mold;
   (c) clamping the opposed ends of the parison in a tensioning fixture;
   (d) heating the mold to a temperature above the glass transition temperature of the polymeric composition;
   (e) simultaneously inflating and longitudinally displacing the tensioning fixture relative to the mold to thereby stretch the parison to form a balloon within the mold cavity and thereby form a balloon having a generally cylindrical center segment, a pair of opposed generally conical end segments and a pair of opposed shaft segments;
   (f) subjecting the balloon of step (e) to a further longitudinal stretch within the heated mold to draw polymeric material from the generally conical end sections without appreciable thinning of the central section thereof, the spacing of the opposed ends of the mold and the arcuate boundary configuration of the general conical end segments configured to affect selective thinning of the balloon cone and shaft segments relative to the central portion;

(g) cooling the mold back down below the glass transition temperature of the polymeric composition; and (h) removing the balloon from the mold.

11. The method as in claim 10 wherein the mold cavity includes arcuate boundaries defining the opposed conical end sections.

12. The methods as in claim 11 wherein the arcuate boundaries are tangent at one end to a segment defining the central section of the balloon and intersect the segment defining the balloon shaft at another end.

13. The method as in claim 10, further comprising the step of heating the mold to the crystallizing temperature of the polymeric composition prior to cooling the mold.

* * * * *